(12) United States Patent
Koike

(10) Patent No.: US 6,786,686 B1
(45) Date of Patent: Sep. 7, 2004

(54) NUMERICALLY CONTROLLED MACHINE TOOL

(75) Inventor: Shinji Koike, Kanagawa (JP)

(73) Assignee: Makino Milling Machine Co., Ltd., Tokyo (JP)

( * ) Notice: Subject to any disclaimer, the term of this patent is extended or adjusted under 35 U.S.C. 154(b) by 0 days.

(21) Appl. No.: 09/889,489

(22) PCT Filed: Nov. 19, 1999

(86) PCT No.: PCT/JP99/06493
§ 371 (c)(1),
(2), (4) Date: Jul. 17, 2001

(87) PCT Pub. No.: WO01/38042
PCT Pub. Date: May 31, 2001

(51) Int. Cl.[7] .......................... B23D 7/00; D23Q 3/157
(52) U.S. Cl. ..................... 409/235; 409/137; 409/211; 29/33 P; 29/563
(58) Field of Search ................. 29/33 P, 563, 29/564; 409/221, 222, 158, 159, 164, 198, 189, 165, 168, 172, 137, 235, 211; 414/808, 800, 802; 248/429; 384/42

(56) References Cited

U.S. PATENT DOCUMENTS

| | | | |
|---|---|---|---|
| 3,200,470 A | | 8/1965 | Muller |
| 3,998,127 A | | 12/1976 | Romeu |
| 4,652,190 A | * | 3/1987 | Corsi ........................ 409/137 |
| 4,921,378 A | * | 5/1990 | Kytola ....................... 409/221 |
| 5,172,464 A | * | 12/1992 | Kitamura et al. ............ 29/563 |
| 5,220,715 A | | 6/1993 | Otani et al. |
| 5,265,986 A | * | 11/1993 | Prokopp ....................... 408/3 |
| 5,301,788 A | * | 4/1994 | Hironaka et al. ......... 198/346.1 |
| 5,321,874 A | * | 6/1994 | Mills et al. ................ 29/33 P |
| 5,564,483 A | | 10/1996 | Sacchi |
| 5,662,568 A | * | 9/1997 | Lindem ........................ 483/30 |
| 5,868,545 A | * | 2/1999 | Kasai et al. ................ 414/808 |
| 5,933,933 A | | 8/1999 | Fritz et al. |
| 6,210,086 B1 | * | 4/2001 | Lecornet et al. ............ 409/137 |
| 6,264,590 B1 | * | 7/2001 | Ferrari ........................ 483/13 |

FOREIGN PATENT DOCUMENTS

| | | |
|---|---|---|
| CH | 585 083 A | 2/1977 |
| EP | 0 904 890 A | 3/1999 |
| JP | 2000-61755 | 2/2000 |

* cited by examiner

Primary Examiner—A. L. Wellington
Assistant Examiner—Dana Ross
(74) Attorney, Agent, or Firm—Paul & Paul

(57) ABSTRACT

A numerically controlled machine tool is disclosed including a spindle support structure for moving the spindle having a tool mounted thereon in directions along an X-axis, a Y-axis and a Z-axis, a workpiece support structure having an indexing workpiece mounting table, and a chip discharge means located between the spindle support structure and the workpiece support structure for discharging chips produced in the machining area to the outside. Since the workpiece mounting table is allowed for rotational indexing, the setup process for the workpiece can be performed with the workpiece mounting surface of the workpiece mounting table facing upward, and therefore the setup process can be shortened while at the same time improving the machine operating rate. Also, since the spindle support structure, the workpiece support structure and the chip discharge means can be configured separately from each other, the machine tool can be manufactured and installed easily.

11 Claims, 11 Drawing Sheets

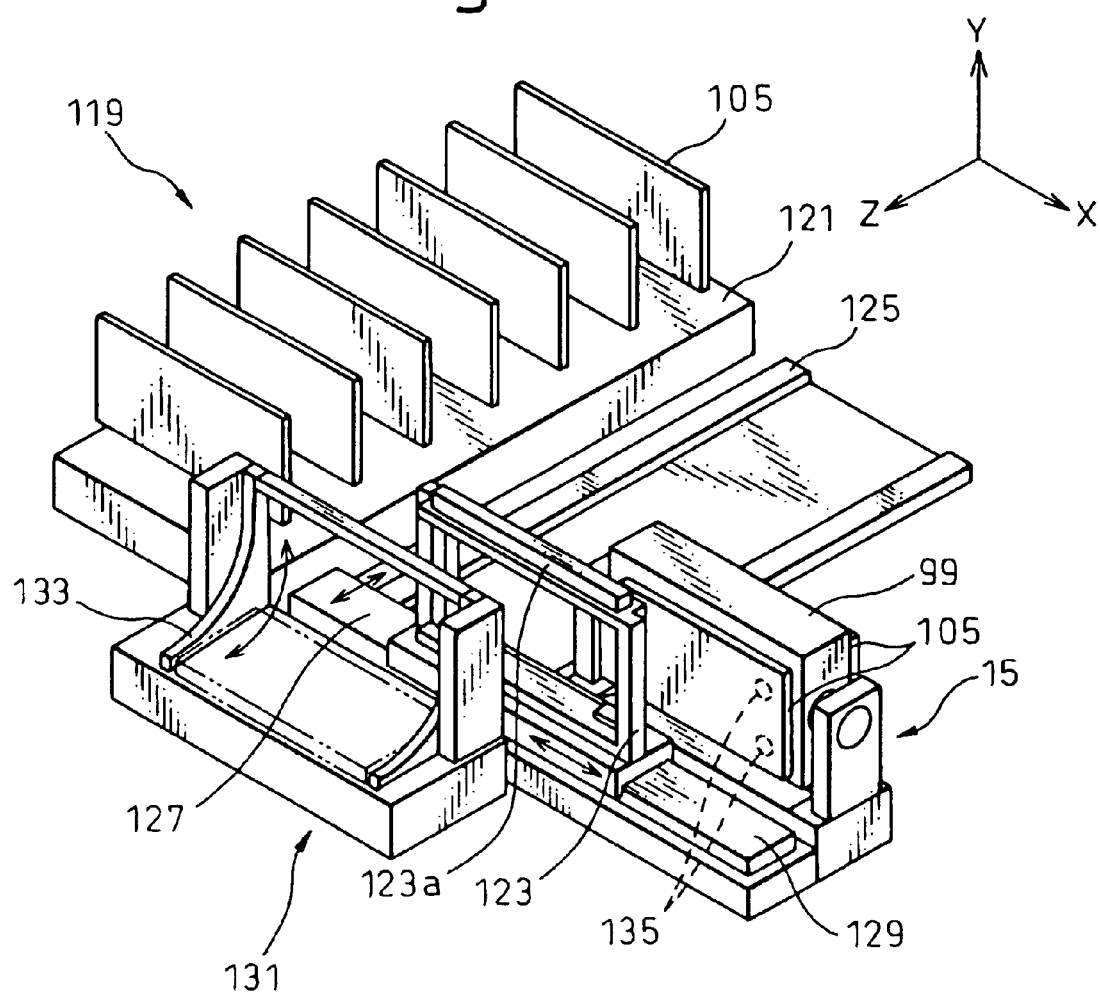

NUMERICALLY CONTROLLED MACHINE TOOL

TECHNICAL FIELD

The present invention relates to a numerically controlled machine tool for machining a large workpiece such as an aircraft part mounted on a workpiece support unit by moving a spindle having a tool mounted thereon in the directions along an X-axis, a Y-axis and a Z-axis with respect to the workpiece.

BACKGROUND ART

In production of an airframe of an aircraft, a method has been conventionally employed in which component parts of the airframe are divided into a plurality of segments and the segments are machined and joined with each other with bolts and rivets. In recent years, however, the trend is toward integrating these parts as far as possible and thereby reducing the jointed portions. As a result, the parts to be machined have increased in size and have become complicated in shape, thereby giving rise to the demand for a novel machine tool for machining such parts.

The unique performance requirements of such a machine tool include the provision of a table on which a large workpiece can be mounted, the provision of a sufficient long stroke in feed axes to machine a large workpiece and the possibility of machining a large part having a complicated shape at any points and in any kind of shapes by a single setup. Further, such parts are required to be machined efficiently, at high speed and with high accuracy. Also, in view of fact that a desired size of a workpiece to be machined varies from one machine tool user to another, the machine tool of a size required by each user can preferably be produced and installed in the factory quickly and at an appropriate time.

For the purpose of fixedly mounting a large workpiece, the table of the machine tool must be large, and it is necessary to take into consideration that the movability of the large table in the directions along three orthogonal linear feed axes, i.e., an X-axis, a Y-axis and a Z-axis, or in the directions along three rotational feed axes, i.e., an A-axis, a B-axis and a C-axis, is disadvantageous from the viewpoint of ensuring the high-speed, high-accuracy machining. Therefore, a machine tool for machining a large part, unlike normal machine tools, is required to have a fixed table and also requires that the spindle rotating with the tool held thereon is provided with orthogonal linear feed units and rotational feed units and is thereby movable in the directions along orthogonal linear feed axes and in the directions along rotational feed axes.

In addition, since a large workpiece is liable to deteriorate an efficiency of a workpiece setup process, the table for fixedly mounting the workpiece thereon is required to include means for automatically changing the workpiece for improving an efficiency of the setup process and an operating rate of the machine tool.

It is noted that the X-axis and the Y-axis are orthogonal to each other in a vertical plane, and extend horizontally and vertically, respectively, while the Z-axis extends in a horizontal direction perpendicular to both the X-axis and the Y-axis. It is also noted that the directions along the A-axis, the B-axis and the C-axis are defined as the directions of rotation about the X-axis, the Y-axis and the Z-axis, respectively.

A first prior art available for satisfying these requirements is a symmetric multiaxial linear motor machine tool described in Japanese Unexamined Patent Publication (Kokai) No. 8-318445. The machine tool includes a vertical gantry movable in a direction along the X-axis on vertically opposed frames, a saddle movable in a direction along the Y-axis on the vertical gantry, a ram adapted to be movable in a direction along the Z-axis on the saddle, a spindle head disposed at the front end portion of the ram for rotatably supporting a spindle having a tool mounted thereon, and a table fixed on the front portion of the frame for mounting a workpiece thereon. The X-, Y- and Z-slides are driven in the feed directions along the X-, Y- and Z-axes by linear motors. The vertical gantry is guided on two sides, upper side and lower side, with respect to the frame and driven by the linear motors. The arrangement of a stator (static element) and a mover (moving element) of the linear motor is symmetrical on the upper and lower sides of the frame so that the attraction forces of the stators acting on the movers, in both the upper and lower linear motors, are vertically offset from each other.

A second available prior art is a machine tool described in Japanese Unexamined Patent Publication No. 9-262727. The machine tool includes a vertical bed in the shape of a rectangular frame having a through opening at the center thereof in front view, an X-slide in the shape of a rectangular frame movable in a direction along the X-axis on the front side of the vertical bed and having a through opening at its center in front view, a Y-slide adapted to be movable in a direction along the Y-axis while being supported and guided in the through opening of the X-slide, a Z-slide adapted to be movable in a direction along the Z-axis while being supported and guided by the Y-slide, a spindle head disposed at the front end portion of the Z-slide for rotatably supporting a spindle having a tool mounted thereon, and a table fixed on the front portion of the vertical bed for mounting a workpiece thereon. The X-, Y- and Z-slides are guided by a pair of rail-shaped guides and driven in the feed directions along the X-, Y- and Z-axes by a pair of linear motors.

Further, a third available prior art is a workpiece pallet exchange method described in Japanese Unexamined Patent Publication No. 60-29261. The machine tool with a pallet changer disclosed in this patent publication includes a machine body for machining a workpiece by relative movement in directions along the X-, Y- and Z-axes between a spindle head for rotatably supporting a spindle having a tool mounted thereon and a table for mounting the workpiece thereon, and a pallet changer disposed adjacent to the machine body for giving and receiving the pallets to/from the table to exchange them. The pallet changer has a plurality of surfaces for mounting pallets thereon and is so structured to rotate about a horizontal rotational axis and thereby to index a w pallet change position, a standby position or a workpiece cleaning position.

As described above, a large machine tool for machining a large part such as a machine tool for machining aircraft parts is generally provided with a fixed, immovable table for mounting a large workpiece thereon, and a rotating spindle thereof having a tool held thereon is provided with an orthogonal linear feed units and/or rotational feed units, thereby allowing for the movement of the spindle in the directions along the X-, Y- and Z-axes and the rotation thereof in the directions along the A-, B- and C-axes. In addition, such machine tool generally has a horizontal spindle, which can move in a relatively long stroke along the X- and Y-axes. Therefore, a tall, large column is moved by being guided on the bed in the horizontal direction along the X-axis while the spindle head moves on the column in the direction along the Y-axis.

As described above, the larger workpiece results in an increased time for the setup process including operations of mounting the workpiece on the table and removing chips from the workpiece or demounting the workpiece from the table after machining. Therefore, during the setup process, the operation of the machine tool is inevitably stopped, thereby resulting in the problem of a low machine operating rate. Further, a movable body (for example, the spindle head and the column) moved in the direction along the X-axis is unavoidably larger and heavier. This makes it difficult to feed the movable body at high speed and also causes another problem of making it difficult to maintain a high positional accuracy in direction along the X-axis due to friction resistance caused by the weight of the movable body moved in the direction along the X-axis.

A method for solving the problem of the reduced working efficiency and the low machine operating rate due to the longer time consumed for the setup process is to add a pallet changer, as described in Japanese Unexamined Patent Publication No. 60-29261, to the machine tool. In view of the need to handle a large workpiece, however, such machine tool requires a larger installation space and a larger-scale structure which in turn causes another problem of a considerably high cost.

On the other hand, a method conceivable for solving the problem of the larger, heavier movable body of the spindle support structure is to use a machine tool described in Japanese Unexamined Patent Publication No. 8-318445 or No. 9-262727 described above, in which a base is constituted of a frame structure having upper and lower X-axis guides for guiding an X-axis slide of a similar frame structure at two upper and lower X-axis guides. Guiding and driving the movable body at upper and lower sides as described above can avoid a cantilevered state of the movable body, thereby making it possible to ensure a movable body having a relatively lighter weight but a required rigidity. Further, a high-speed feed can be achieved by using linear motors as a means for driving the movable body.

However, a new particular problem is caused by a machine tool requiring a longer stroke in a direction along the X-axis than a standard machine tool. More specifically, the longer length of stroke along the X-axis can require a longer movable cover of a telescopic type or a take-up type covering the feed mechanism and the guide along the X-axis for protection from the chips produced from the workpiece by machining process, and this longer movable cover often develops a malfunction. This problem is indicated in neither Japanese Unexamined Patent Publication No. 8-318445 nor No. 9-262727 which is not intended for a machine tool having a relatively longer stroke in the direction along the X-axis. Also, in spite of the lighter X-axis slider, the longer stroke in the direction along the Y-axis imposes some degree of load on the X-axis guide, thereby giving rise to the need of ensuring a safety factor over the service life thereof.

DISCLOSURE OF THE INVENTION

The present invention has been developed in view of these problems, and the object thereof is to provide a numerically controlled machine tool capable of machining a large workpiece at high speed with high accuracy and of facilitating the setup process for a large workpiece. Another object of the present invention is to provide a numerically controlled machine tool for machining a large workpiece with a high machine operating rate. Still another object of the present invention is to provide a numerically controlled machine tool having a long stroke along the X-axis which can be easily manufactured and installed. Yet another object of the present invention is to provide a numerically controlled machine tool for machining a large workpiece in which chips can be easily disposed of.

According to a first aspect of the present invention, there is provided a numerically controlled machine tool for machining a workpiece mounted on a workpiece support unit by moving a spindle having a tool mounted thereon in directions along an X-axis, a Y-axis and a Z-axis with respect to the workpiece, which comprises: a spindle support structure including a base adapted to be located on a floor surface and having guides extending in the direction along the X-axis on the upper and lower portions thereof, an X-axis slider guided along the guides on the upper and lower portions of the base to move from side to-side in the direction along the X-axis, a Y-axis slider guided to move upwardly and downwardly in the direction along the Y-axis on the X-axis slider, a Z-axis slider guided to move forwardly and backwardly in the direction along the Z-axis on the Y-axis slider, and a spindle head fixedly mounted on the Z-axis slider or mounted to be rotatable in at least one of directions along an A-axis, a B-axis and a C-axis; a workpiece support structure including a base having spindle support means located at the opposing ends thereof along the X-axis and a workpiece mounting table supported by the spindle support means to allow for rotational indexing about the horizontal axis extending in the direction along the X-axis and having at least one workpiece mounting surface; and a chip discharge means located between the spindle support structure and the workpiece support structure for discharging chips produced in the machining area to the outside of the machining area.

According to an embodiment of the aforementioned numerically controlled machine-tool, the base of the spindle support structure may be configured of an extended base having a plurality of base units coupled to each other along the X-axis, the base unit having a predetermined X-axis unit length, and the workpiece support structure may be configured of an extended workpiece support structure having a plurality of workpiece support structure units coupled to each other along the X-axis with the horizontal axes thereof aligned, the workpiece support structure having a predetermined X-axis unit length.

In the aforementioned embodiment, the X-axis slider of the spindle support structure may be driven in the direction along the X-axis by linear motors disposed along the guides on the upper and lower portions of the base, and the linear motor may include a stator and a mover arranged on the base and the X-axis slider, respectively, in opposed relation to each other so that an attraction force of the stator acting on the mover may reduce the load in gravitational direction exerted on the guide of the X-axis slider.

Further, according to the aforementioned embodiment, the base of the spindle support structure may have longitudinal spaces extending in the direction along the X-axis and opening downwardly in the upper and lower portions of the base, respectively, and each of the longitudinal spaces may accommodate therein a guide for guiding and supporting the X-axis slider and an X-axis feed means for moving the X-axis slider in the direction along the X-axis.

In the aforementioned embodiment, preferably, the workpiece mounting table of the workpiece support structure is formed into a shape of a substantially triangle pole having three workpiece mounting surfaces extending in parallel to the horizontal axis in the direction along the X-axis. Preferably, the workpiece support structure is also provided with a pushing means located between the bottom of the workpiece mounting table and the base for imparting an upward pushing force on the workpiece mounting table.

According to a second aspect of the present invention, there is provided a numerically controlled machine tool for machining a workpiece mounted on a workpiece support unit by moving a spindle with a tool mounted thereon in directions along an X-axis, a Y-axis and a Z-axis with respect to the workpiece, which comprises: a spindle support structure including a base adapted to be located on a floor surface and having guides extending in the direction along the X-axis on the upper and lower portions thereof, an X-axis slider guided along the guides on the upper and lower portions of the base to move from side to side in the direction along the X-axis, a Y-axis slider guided to move upwardly and downwardly in the direction along the Y-axis on the X-axis slider, a Z-axis slider guided to move forwardly and backwardly in the direction along the Z-axis on the Y-axis slider, and a spindle head fixedly mounted on the Z-axis slider or mounted to be rotatable in at least one of directions along an A-axis, a B-axis and a C-axis; a workpiece support structure including a base having shaft support means located at the opposing ends thereof along the X-axis, and a workpiece mounting table supported by the shaft support means to allow rotational indexing about a horizontal axis extending in the direction along the X-axis and having at least one pallet mounting means for detachably mounting on the workpiece mounting table a pallet for attaching a workpiece thereon; a pallet changing means including a pallet stocker located adjacent to the workpiece support structure and a pallet carrier for transporting the pallet between the workpiece mounting table and the pallet stocker; and a chip discharge means located between the spindle support structure and the workpiece support structure for discharging chips produced in the machining area to the outside of the machining area.

According to a third aspect of the present. invention, there is provided a numerically controlled machine tool for machining a workpiece mounted on a workpiece support unit by moving a spindle having a tool mounted thereon in directions along an X-axis, a Y-axis and a Z-axis with respect to the workpiece, which comprises: a spindle support structure including a base adapted to be located on a floor surface and having guides extending in the direction along the X-axis on the upper and lower portions thereof, an X-axis slider guided along the guides on the upper and lower portions of the base to move from side to side in the direction along the X-axis, a Y-axis slider guided to move upwardly and downwardly in the direction along the Y-axis on the X-axis slider, a Z-axis slider guided to move forwardly and backwardly in the direction along the Z-axis on the Y-axis slider, and a spindle head fixedly -mounted on the Z-axis slider or mounted to be rotatable in at least one of directions along an A-axis, a B-axis and a C-axis; and a workpiece rest disposed in the front surface of the spindle support structure for fixedly mounting a workpiece thereon, wherein the base of the spindle support structure is provided with longitudinal spaces extending in the direction along the X-axis and opening downwardly in the upper and lower portions of the base, respectively, the guide located in each of the longitudinal spaces for guiding and supporting the X-axis slider, and an X-axis feed means located along the guide in each of the longitudinal spaces for moving the X-axis slider. In the numerically controlled machine tool described above, preferably, the X-axis feed means is configured of a linear motor including a stator, and the X-axis slider is provided with wiper means for removing dust or chips attached to the guide and the stator of the linear motor.

In the spindle support structure, the X-axis slider constituting one of the components of the movable body capable of moving with respect to the stationary base is guided and supported at the upper and lower edge portions thereof so that the force exerted on the X-axis slider (thrust force and support force) is applied to substantially symmetrical points. As a result, unlike a cantilevered X-axis slider, the X-axis slider is not required to be reinforced by a structural member in order to prevent the distal end portion from being bent or deflected due to a generated moment. The structure can thus be reduced in weight and can be moved at high speed. Generally, a machine tool, especially a machine tool for machining a large workpiece has a long stroke along the direction of the X-axis. Therefore the movable body capable of moving at high speed in the direction along the X-axis greatly contributes to a higher machining rate for the machine tool as a whole and a shorter operating time,-thereby making it possible to improve the efficiency of the machining process.

Further, the provision of the workpiece mounting table supported to be allowed for rotational indexing about the horizontal axis extending in the direction along the X-axis allows the workpiece mounting surface to be set in a position where the surface faces upward or preferably in horizontal position, thus facilitating the setup process. The resulting shortened setup time contributes to an improved operating rate for the machine.

When the workpiece mounting table is provided with pallet mounting means, the workpiece mounting table, in combination with the pallet changing means, makes it possible to automate the job of changing the pallet. Thus, the job of changing the pallet with the workpiece mounted thereon can be improved in efficiency, resulting in an improved efficiency of the machining process.

Further, the longitudinal space formed in the base of the spindle support structure and opening downwardly protects the guides, the linear motors or the feeding means such as the ball screw from chips and therefore eliminates the need of the movable cover normally arranged on the X-axis guide. Hence, this is also effective for reducing the loss of the power for X-axis feed and contributes to an increased speed of the X-axis slider in the direction along the X-axis.

When the X-axis slider is driven by a linear motor, the movement in the direction along the X-axis can be increased in speed. By arranging the stator and the mover of the linear motor to reduce the load in the gravitational direction exerted on the guide of the X-axis slider, on the other hand, the friction resistance of the guide is reduced and thus the speed can be further increased. The service life of the guides and the slide element is also longer.

The chip discharge means is intended to reduce the job of removing chips by discharging into a predetermined place the used cutting fluid and the chips that have been produced in the machining area and naturally dropped. Further, the chip discharge means is arranged to separate the spindle support structure and the workpiece support structure from each other. This arrangement facilitates the production and installation of a large machine tool, while at the same time making it possible to make the spindle support structure and the workpiece support structure modular units. The spindle support structure and the workpiece support structure are of course required to be indirectly coupled to each other by concrete or metal members arranged on the floor.

By combining the effects presented by the configuration described above, the numerically controlled machine tool according to the present invention can shorten the setup process time and the machining time, thereby improving the efficiency of the machining process as a whole.

BRIEF DESCRIPTION OF THE DRAWINGS

The above and other features and advantages of the present invention will become more apparent from the following detailed description of the invention taken in conjunction with the accompanying drawings, wherein:

FIG. 13 show an embodiment of a pallet changing means combined with a workpiece support structure of a numerically controlled machine tool according to the present invention.

BEST MODE FOR CARRYING OUT THE INVENTION

Figure 1:
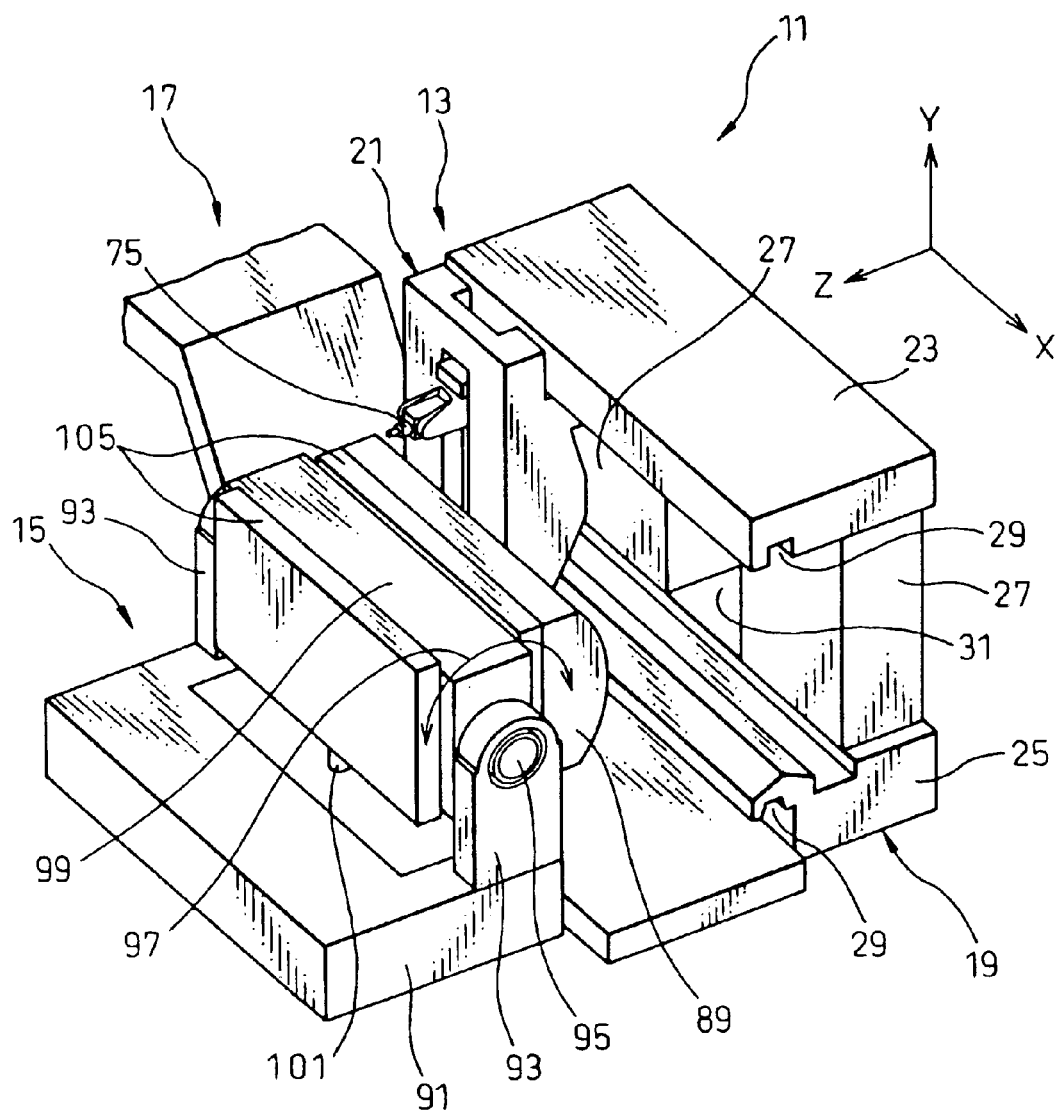
FIG. 1 is a diagram showing a general configuration of a numerically controlled machine tool according to the present invention.
Figure 2:
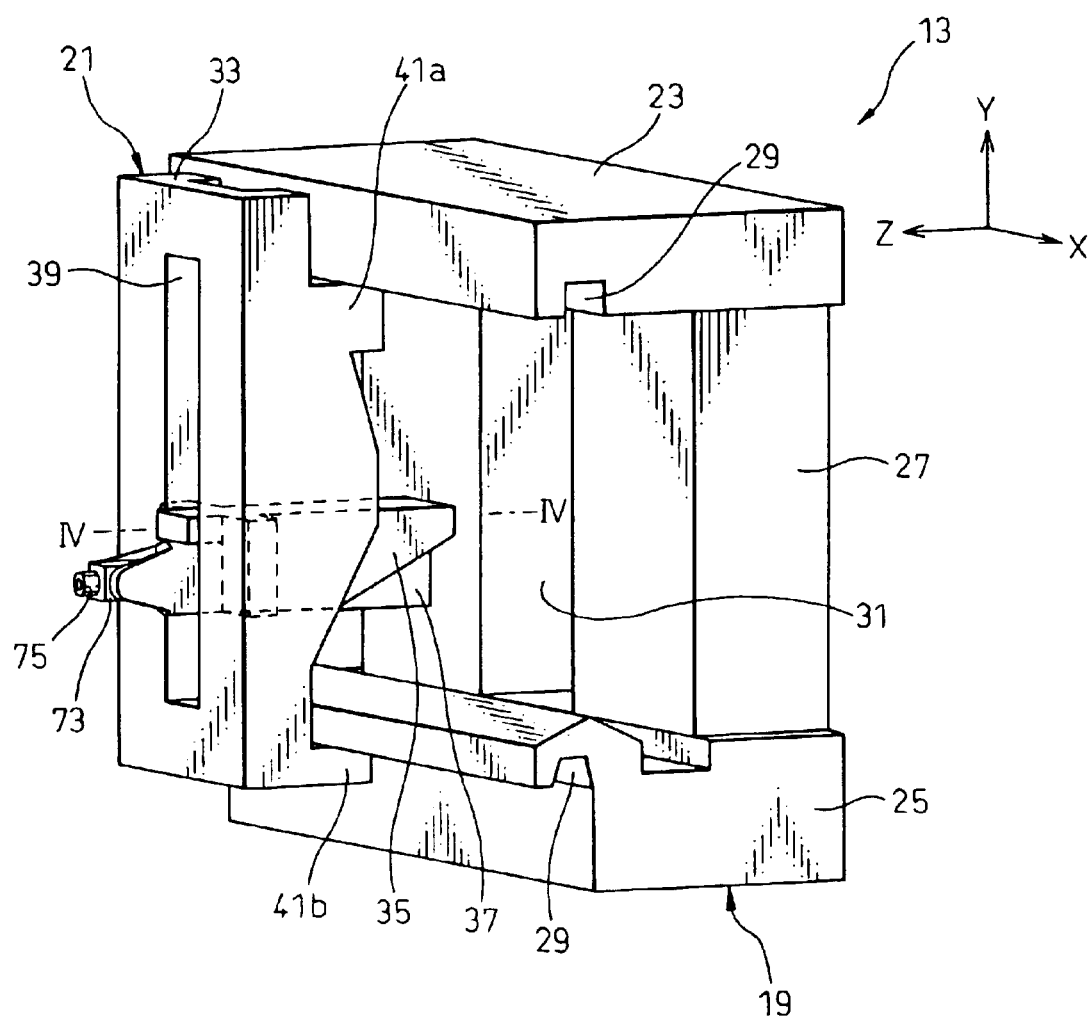
FIG. 2 is a perspective view showing a spindle support structure of the numerically controlled machine tool shown in FIG. 1.

FIG. 1 is a diagram showing a general configuration of a numerically controlled machine tool 11 according to the present invention. The numerically controlled machine tool 11 shown in FIG. 1 is configured with a spindle support structure 13, a workpiece support structure 15 and a chip discharge means 17 interposed between the spindle support structure 13 and the workpiece support structure 15. FIG. 2 is a perspective view of the spindle support structure 13 shown in FIG. 1.

In the following description, it should be noted that, unless otherwise specified, the front side of the machine tool refers to a side performing a machining function, and the rear side of the machine tool refers to the opposite side far away from the side performing the machining function. It should also be noted that, as shown in FIG. 1, the longitudinal direction of the machine tool is defined as a direction along an X-axis, the direction extending vertically is defined as a direction along a Y-axis, and the direction perpendicular to the X-axis and the Y-axis is defined as a direction along a Z-axis.

Referring to FIGS. 1 and 2, the spindle support structure 13 includes a base 19 located on the floor surface and a movable body 21. The base 19 further includes a beam 23 at the top thereof, a bed 25 at the bottom thereof, and a column 27 on the rear side thereof which connects the beam 23 and the bed 25. Therefore the base 19 has a C-shape in section as viewed from the side thereof. Each of the beam 23 and the bed 25 is formed with a groove-shaped longitudinal space 29 extending at the front portion thereof in the direction along the X-axis. Preferably, the groove-shaped longitudinal space 29 is formed to open downwardly as shown in FIGS. 1 and 2.

The column 27 connects the beam 23 and the bed 25 and reinforces a rigidity of the beam 23 by supporting the beam 23 not to be deformed in the direction along the X-axis. However, as long as the beam 23 can maintain a sufficient rigidity to cause no deformation in the direction along the X-axis, the column 27 may be formed with an opening 31, as shown in FIGS. 1 and 2, or be constituted of a plurality of post members spaced apart from each other. The provision of the opening 31 can reduce the weight of the spindle support structure 13. The opening 31 is of course not required in the case where a large rigidity is required.

Referring to FIG. 2, the movable body 21 includes an X-axis slider 33 guided to be movable from side to side in the direction of the X-axis along the longitudinal space 29 of the base 19, a Y-axis slider 35 guided to be movable upwardly and downwardly in the-direction of the Y-axis on the X-axis slider 33, and a Z-axis slider 37 guided to be movable forwardly and backwardly in the direction of the 2 -axis on the Y-axis slider 35.

The X-axis slider 33 is formed into a frame shape with an elongate through opening 39 extending along the direction of the Y-axis at the center in front view, and has extensions 41a, 41b projecting into the upper and lower grooved-shaped longitudinal spaces 29 of the base 19 from the upper and lower portions thereof, respectively. The X-axis slider 33 is moved along the longitudinal space 29 of the extensions 41a, 41b by X-axis feed means. The X-axis feed means can be, for example, a combination of a motor and a ball screw or a linear motor.

Figure 3:
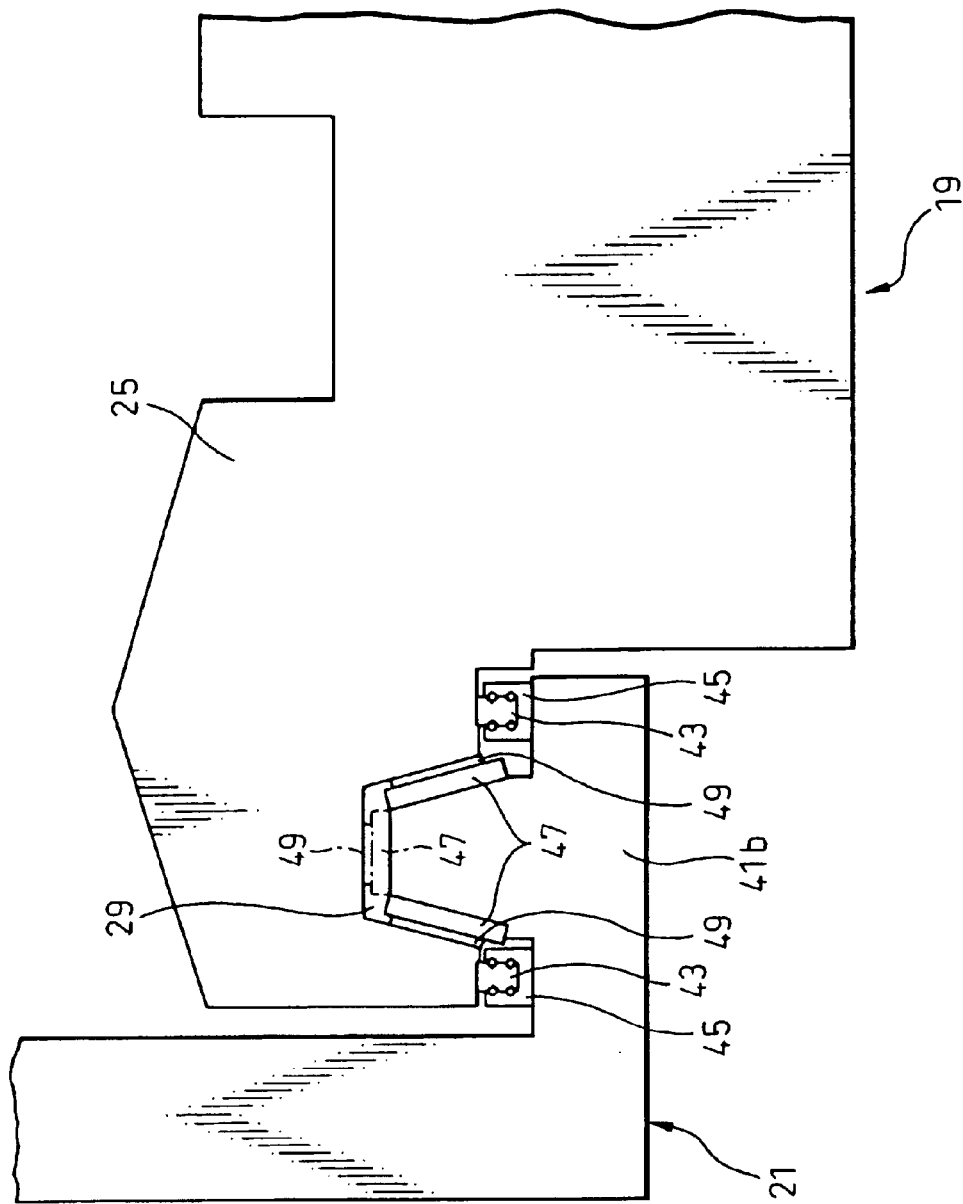
FIG. 3 is a side view of a lower front end portion of a base of the spindle support structure shown in FIG. 2.

Referring to FIG. 3 showing a side view of the front end portion of the lower portion (bed 25) of the base 19 shown in FIG. 2, the bed 25 is provided at the front end portion with two rail-shaped X-axis guides 43 extending in parallel in the direction of the X-axis with the opening area of the longitudinal space 29 interposed therebetween. The extension 41b of the X-axis slider 33 is provided with a plurality of X-axis slide elements 45 having rolling members adapted to engage with the X-axis guides 43 so that the X-axis slider 33 can be guided in the direction along the X-axis by means of the X-axis guide 43 and the X-axis slide elements 45.

On the other hand, one or more movers (moving element) 47 of a linear motor, i.e., X-axis feed means, are disposed in the forward end portion of the extension 41b extending from the extension 41b into the longitudinal space 29 of the bed 25, and one or more stators 49 of the linear motor are disposed in opposed relation to the movers 47 on the surface of the bed 25 surrounding the longitudinal space 39.

By providing the X-axis guides extending in parallel with the opening area of the longitudinal space 29 interposed therebetween, the extension 41b can be avoided from being formed as a cantilevered portion, thereby ensuring the rigidity required for the extension.

Similarly, X-axis guides 43 and X-axis slide elements 45 as well as one or more movers 47 and one or more stators 49 of a linear motor are disposed on the extension 41a in the upper portion of the X-axis slider 33 and on the surface of the beam 23 surrounding the longitudinal space 29 formed in the beam 23 at the top of the base 19, respectively.

In the aforementioned embodiment, the two X-axis guides 43 are disposed with the opening area of the longitudinal space 29 interposed therebetween, although a single X-axis guide can replace them. A guide of other types such as a sliding surface can be also used in place of the rail-shaped X-axis guide 31. Further, a combination of a motor and a ball screw can be used as the X-axis feed means in place of the linear motor.

This configuration allows the movable body 21 to move in the direction of the X-axis on the base 19 by being driven by means of the X-axis feed means arranged in the longitudinal spaces 29 while being guided and supported by the X-axis guides 43 arranged on the beam 23 and the bed 25.

Since the X-axis slider 33 of the movable body 21 moving on the base 21 is supported and guided on two sides at the upper and lower portions, the moment of rotation is not exerted on the X-axis slider 33 like a cantilevered X-axis slider supported and guided on a single side. Therefore, the required rigidity for the X-axis slider 33 can be easily ensured while at the same time reducing the weight of the X-axis slider 33. As a result, a reduced weight of the movable body 21 is achieved, so that the movable body 21 can move at high speed in the direction of the X-axis.

Further, since the longitudinal spaces 29 are open downwardly and accommodate therein a guiding and driving mechanism including the X-axis guides 43 and the X-axis feed means, the guiding and driving mechanism for the X-axis cannot be easily intruded into by the chips and dust produced in the machining area.

If the groove-shaped longitudinal spaces 29 formed in the front end portions of the bed 25 and the beam 23 are open downwardly, it is advantageous that the width of each of the longitudinal spaces 29, as shown in FIG. 3, expands progressively and downwardly so that the cross section thereof is of a trapezoidal shape having symmetric side slopes, and that the forward end portions of the extensions 41a, 41b of the X-axis slider 33 located in the longitudinal spaces 29 are also of a trapezoidal shape. In that case, the stators 49 of the linear motor are arranged on the extensions 41a, 41b along the two side slopes of the trapezoidal forward end portions thereof and the movers 47 of the linear motor are arranged on the X-axis slider 33 in opposed relation to the stator 49.

When the movers 47 and the stators 49 of the linear motor are arranged in this way on the symmetric slopes of the longitudinal spaces 29 and the forward end portions of the extensions 41a, 41b, the attraction force acting between the movers 47 and the stators 49 of the linear motor causes a force in the opposite direction to the gravity to be exerted on the X-axis slider 33. Thus, the force in the opposite direction to the gravitational force exerted on the X-axis slider 33 is exerted on the X-axis slider 33, so that the load exerted by the X-axis slider 33 on the X-axis guide 43 located on the bed through the X-axis slide elements 45 arranged on the X-axis slider 33 is reduced. This reduces the friction resistance between the X-axis slide elements 45 and the X-axis guides 43, thereby making it possible to move the X-axis slider 33 at higher speed. Thus, the positioning accuracy is improved.

By changing the angle of the slope of the inclined surface for mounting the linear motor thereon in the longitudinal space 29 and the forward end portions of the extensions 41a, 41b, the degree of the force reducing the gravitational force exerted on the X-axis slide members 45 can be adjusted without changing the driving force of the linear motor in the direction of the X-axis. Thus, this makes it possible to set the force acting on the X-axis guides 43 from the X-axis slider 33 through the X-axis slide elements 45 at an appropriate value and can lengthen the service life of the X-axis slide elements 45.

Alternatively, like the longitudinal space 29 of the beam 23 shown in FIGS. 1 and 2, each of the longitudinal spaces 29 of the bed 25 and the beam 23 is formed into a shape of a rectangular section and each of the forward end portions of the extensions 41a, 41b of the X-axis slide 33 correspondingly has a rectangular shape in section. In such a case, the stators 49 of the linear motor are arranged along the top surface of the longitudinal space 29, and the movers 49 of the linear motor are arranged on the X-axis slider 33 in opposed relation to the stators 49. Even in this arrangement, the force in the opposite direction to the gravitational force exerted on the X-axis slider 33 is exerted on the X-axis slider 33. Therefore, this arrangement also makes it possible to reduce the force in the direction of the gravity which is exerted on the X-axis guide 43 by the X-axis slider 33 through the X-axis slide elements 45.

Figure 4:
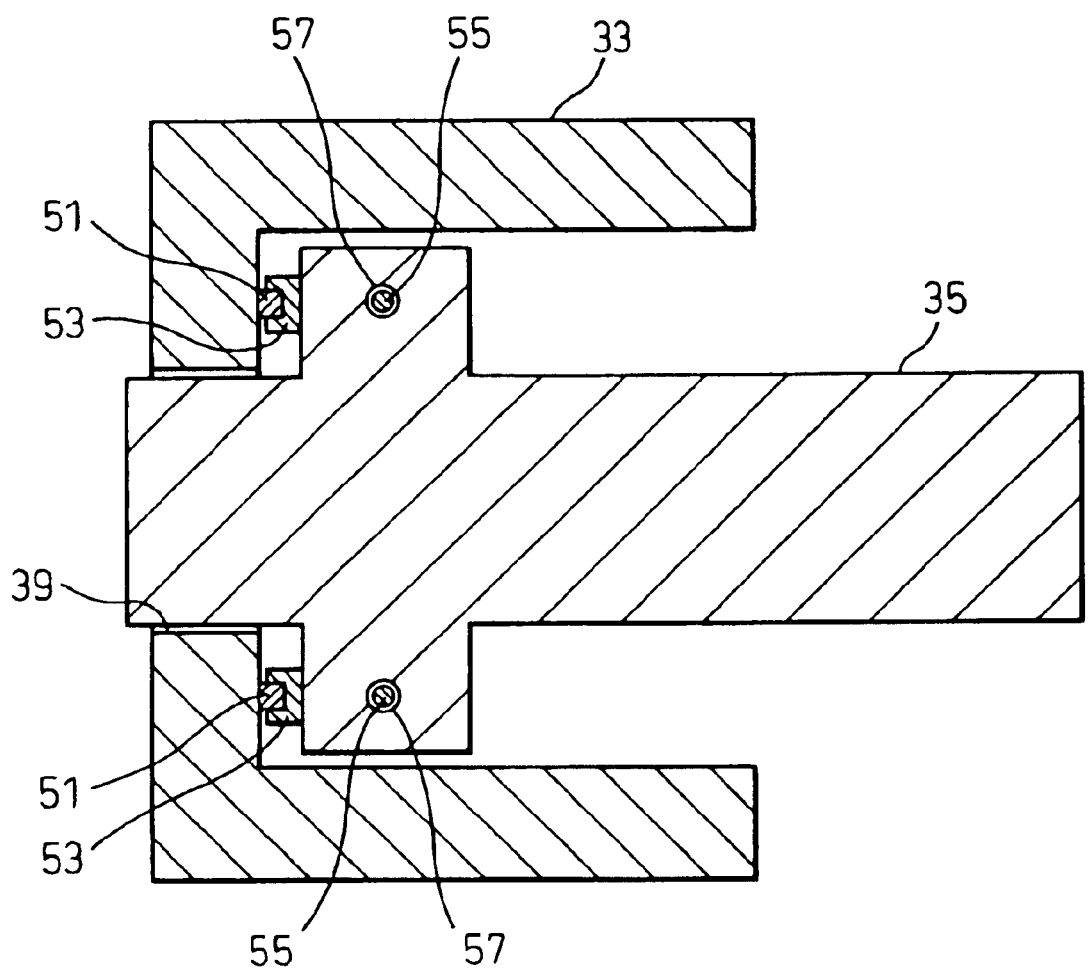
FIG. 4 is a top sectional view taken along the line IV—IV of FIG. 2, showing the X-axis slider and the Y-axis slider of the spindle support structure shown in FIG. 2 as viewed from the top side.

Referring to FIG. 4 which is a sectional view taken along the line IV—IV of FIG. 2 showing the X-axis slider 33 and the Y-axis slider 35 of FIG. 2 as view from the top side, the X-axis slider 33 is provided inside of the through opening with a combination of a motor (not shown) i.e., a Y-axis feed means, with ball screws 55, and rail-shaped Y-axis guides 51. On the other hand, the Y-axis slider 35 is symmetrically provided on the right and left sides Y-axis slide elements 53 in mesh with the rail-shaped Y-axis guides 51 located on the X-axis slider 33, so that the Y-axis slider 35 is guided in the direction of the Y-axis by the Y-axis guides 51 and the Y-axis slide elements 53. Referring to FIG. 4, the ball screws 55 of the Y-axis feed means are also screwed into the threaded holes of nuts 57 (only the threaded holes of the nuts are shown in the drawing) symmetrically arranged on the Y-axis slider 35. Therefore the rotation of the ball screws 55 by a motor (not shown) is transmitted through the nuts 57 to the Y-axis slider 35, which is in turn guided by the Y-axis guides 51 and the Y-axis slide elements 53 to move in the direction along the Y-axis in the through opening 39.

Figure 5:
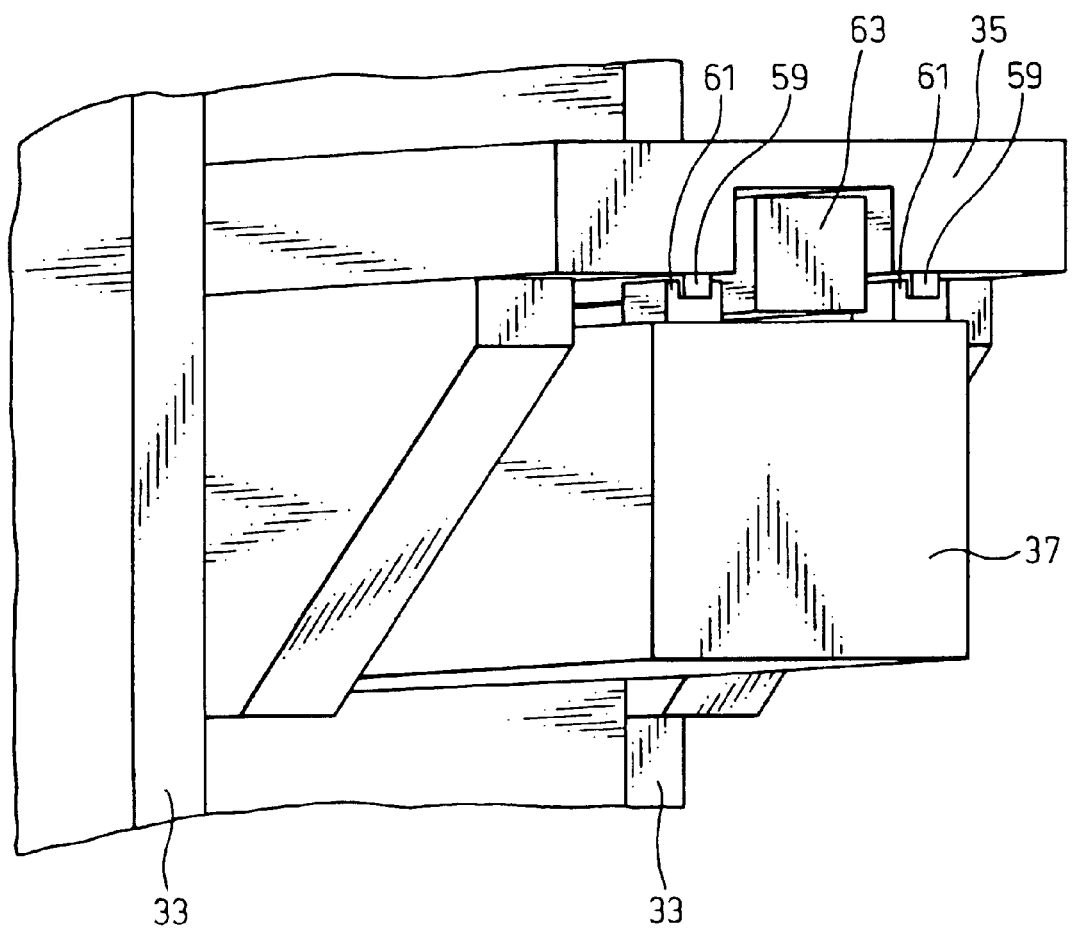
FIG. 5 is a rear perspective view showing the Y-axis slider of the spindle support structure.

Referring to FIG. 5 which is a rear perspective view of the Y-axis slider 35, the Y-axis slider 35 is formed with a space extending therethrough in the direction along the Z-axis, which space accommodates therein a Z-axis slider 37. The space also fixedly accommodates a Z-axis motor 63, i.e. a Z-axis feed means, as well as two rail-shaped Z-axis guides 59.

On the other hand, the Z-axis slider 37 is provided with a Z-axis slide elements 61 in mesh with the Z-axis guides 59 located in the space inside of the Y-axis slider 35. Similarly to the Y-axis slider 35, the rotation of the Z-axis motor 63 mounted on the Y-axis slider 35 is transmitted through ball screws (not shown), so that the Z-axis slider 37 moves in the direction along the Z-axis within the space inside of the Y-axis slider 35.

This allows the movable body 21 to move in the three directions along the X-, Y- and Z-axes.

It should be noted that the Y- and Z-axis feed means are described as a combination of a motor and ball screws, although a linear motor can be used alternatively. The through opening 39 above and below the Y-axis slider 35 are covered with a telescopic cover (not shown) to prevent the intrusion of chips or cutting fluid.

Figure 6:
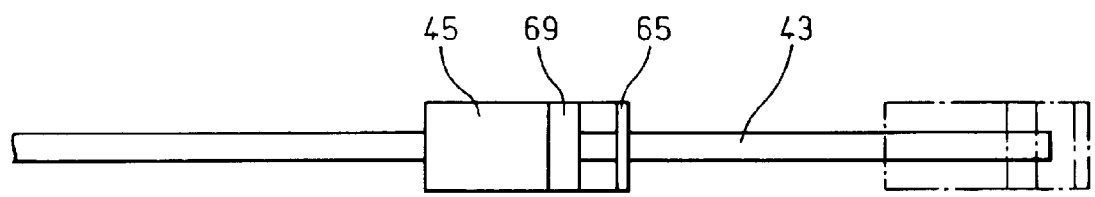
FIG. 6 is a diagram for illustrating a structural relationship of an X-axis guide and an X-axis slide element shown in FIG. 3.
Figure 7:
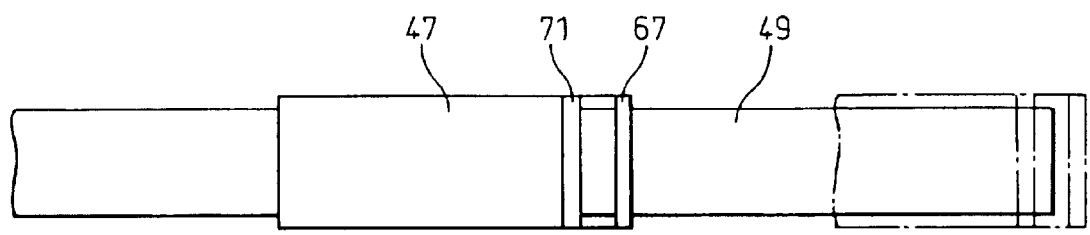
FIG. 7 is a diagram for illustrating a structural relationship of a stator and a mover of a linear motor shown in FIG. 3.

FIG. 6 is a model diagram for illustrating a structural relationship of the rail-shaped X-axis guide 43 and the X-axis slide element 45 shown in FIG. 3, and FIG. 7 is a diagram for illustrating a structural relationship of the mover 47 and the stator 49 of the linear motor shown in FIG. 3.

As shown in FIGS. 6 and 7, wiper means for removing the chips and the cutting fluid attached on the X-axis guides 43 and on the stator 49 of the linear motor can be mounted on the X-axis slide element 45 and the mover 47 of the linear motor arranged at the X-axis ends of the X-axis slider 33. Preferably, the wiper means includes no-contact wipers 65, 67 arranged on the forward end side of the X-axis slide element 45 and on the forward end side of the mover 47 of the linear motor and contact wipers 69, 71 spaced inwardly apart from the no-contact wipers 65, 67. The no-contact wipers 65, 67 are not in direct contact with the X-axis guide 43 or the stator 49 of the linear motor, respectively, but function to remove large chips attached on them. On the other hand, the contact wipers 69, 71 are in direct contact with the X-axis guide 43 or the stator 49 of the linear motor and function to remove fine chips and the cutting fluid attached on them. A polymeric material such as polyurethane impregnated with oil for lubrication can be used for the contact wipers 69, 71. An appropriate material can be used for the no-contact wipers 65, 67.

Such wiper means can of course be disposed at the front and rear ends of the X-axis slide element 45 and the mover 47 of the linear motor.

At the X-axis stroke ends of the X-axis guide 43 and of the stator 49 of the linear motor, as indicated by dashed line in FIGS. 6 and 7, the contact wipers 69, 71 may move to the end of the X-axis guide 43 or the stator 49 of the linear motor while the no-contact wipers 65, 67 may move to a position beyond the end of the X-axis guide 43 or the stator 49 of the linear motor. This configuration allows the chips and the cutting fluid wiped off from the X-axis guide 43 and the stator 49 of the linear motor by the contact wipers 69, 71 and the no-contact wipers 65, 67 to be removed out of the ends of the X-axis guide 43 and the stator 49.

The compressed air may be also blown out of the X-axis slide element 45 or the mover 47 of the linear motor to assist in blowing off the chips and the cutting fluid attached on the X-axis guide 43 or the stator 49 of the linear motor.

The provision of the wiper means such as the contact wipers, the no-contact wipers and the blowout of the compressed air can assure the smooth movement of the X-axis slide element 45 or the mover 47 of the linear motor along the X-axis guide 43 or the stator 49 of the linear motor, respectively, which otherwise might be hampered by the chips caught between the X-axis guide 43 and the X-axis slide element 45 or between the mover 47 and the stator 49 of the linear motor. Thus, the failure frequency of the guiding mechanism or the driving mechanism is reduced for an improved operating rate of the machine tool.

Conventionally, the X-axis guiding and driving mechanism is provided with a movable cover for blocking chip intrusion. The use of this movable cover for a long period of time often causes a malfunction due to bite or wear. However, the need of the movable cover can be eliminated by accommodating the X-axis guides 43, the X-axis slide elements 45, and the mover 47 and the stator 49 of the linear motor in the longitudinal space opening downwardly and by the provision of the wiper means for the X-axis slide element 45 and the mover 47 of the linear motor. Therefore, the machine downtime due to a malfunction caused by the movable cover can be avoided, resulting in an improved operating rate of the machine tool. Another advantage is to reduce a loss of the feed power which has thus far been caused by the movable cover.

Referring to FIG. 2, a spindle head 73 for rotatably supporting the spindle 75 having a tool mounted thereon is held at the front end of the Z-axis slider 37 of the movable body 21.

Figure 8:
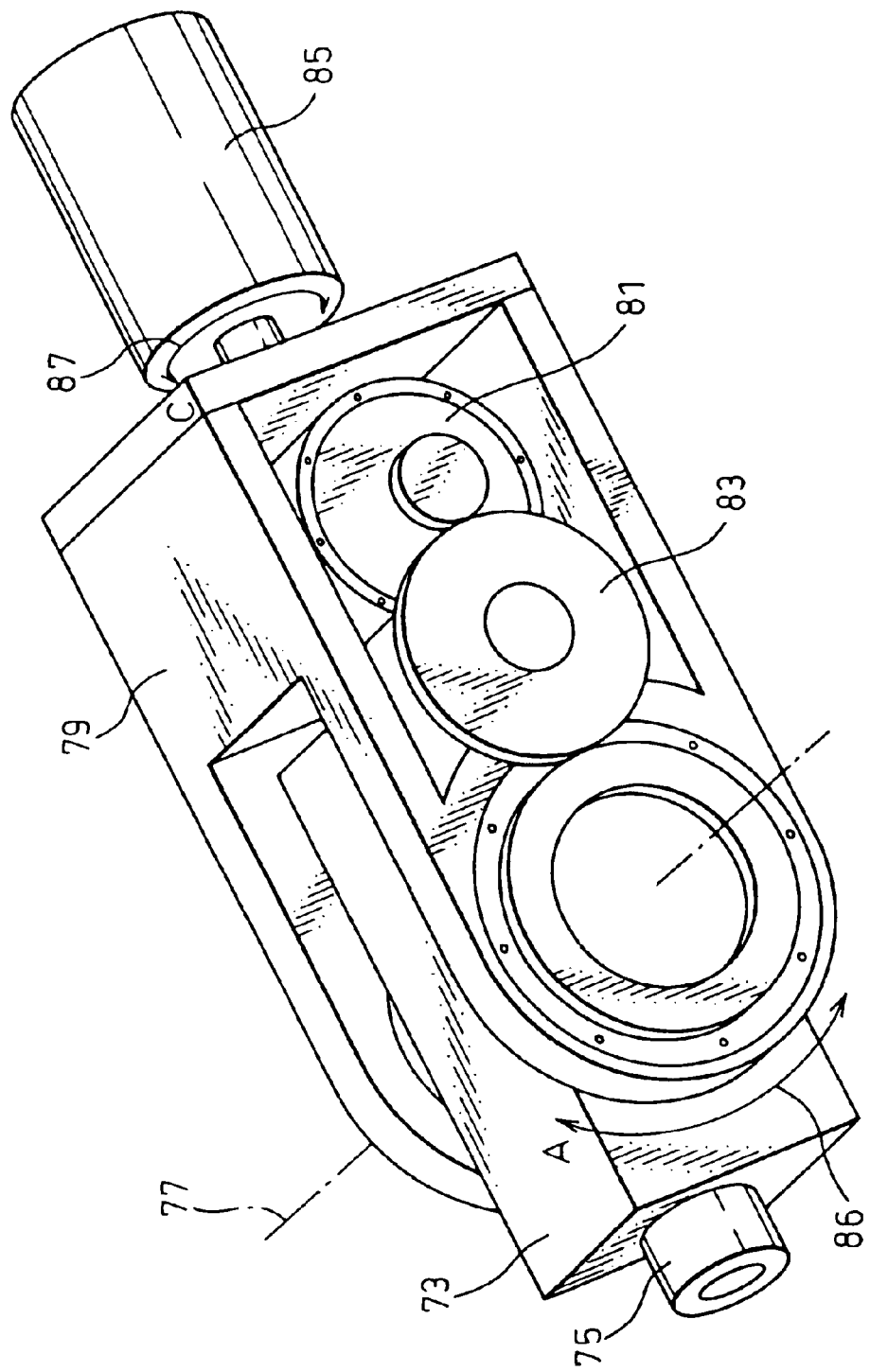
FIG. 8 is a detailed view of the portion including a swivel base and a spindle head shown in FIG. 2.

As shown in FIG. 8 which is the detailed view of the portion including the spindle head 73, the spindle head 73 is rotatably supported on a swivel base 79 in the direction 86 along the A-axis about the rotational axis 77 perpendicular to the direction along the Z-axis, and can be rotated through a gear 83 by a swivel motor 81 fixed on the swivel base 79. The swivel base 79, in turn, is connected to a C-axis motor 85 fixed on the Z-axis slider 37 so that it can be rotated by the C-axis motor 85 in the direction 87 along the C-axis about the rotational axis extending in the direction along the Z-axis. Therefore, the spindle head 73 is rotatable in the directions along the A-and C-axes, thereby making it possible to handle a complicated machining process. The same gear train as the gear 83 is also located on the other side of the swivel base 79 so that the rotational feed drive along the A-axis is carried out on both left and right sides. Thus, a highly accurate rotational feed is possible.

The spindle head 73 may be adapted to be fixedly mounted on the Z-axis slider 37 and to rotate in the direction neither along the A-axis, the B-axis or the C-axis. The spindle 75 may be also movable in the direction along the Z-axis (what is called a W-axis) with respect to the spindle head 73.

Then, the workpiece support structure 15 will be described.

Figure 9:
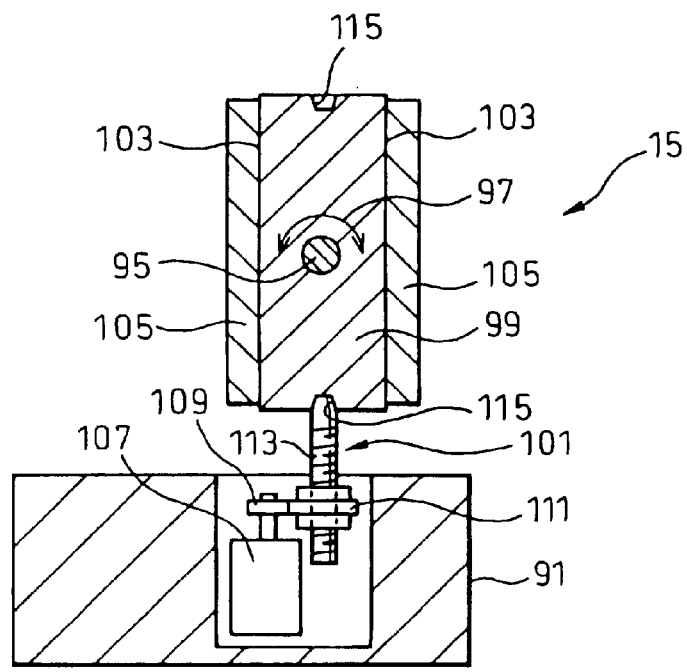
FIG. 9 is a sectional view of a workpiece support structure of FIG. 1 with the workpiece removed therefrom.
Figure 10:
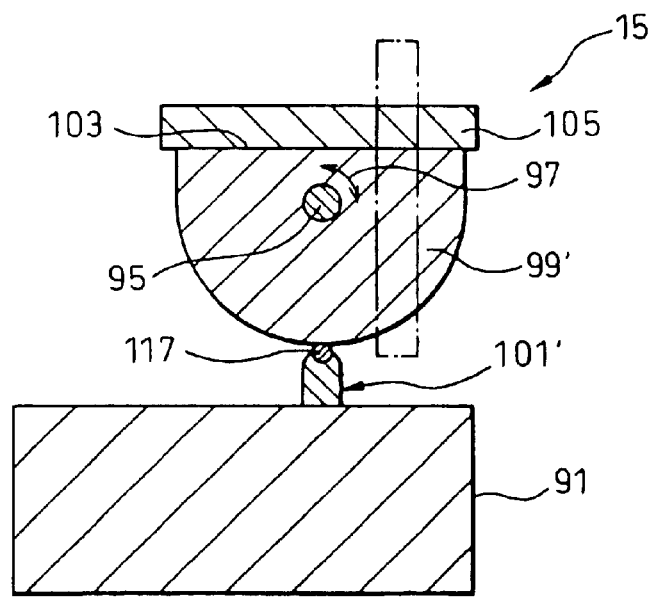
FIG. 10 is a sectional view of a second embodiment of a workpiece support structure similar to FIG. 9.

FIG. 9 is a partial side sectional view of the workpiece support structure 15 shown in FIG. 1 with the workpiece 89 removed from the workpiece support structure 15. FIG. 10 is a partial side sectional view of a second embodiment of a workpiece support structure 15 similar to that of FIG. 9.

Referring FIGS. 1 and 9, the workpiece support structure 15 includes a base 91, two shaft support means 93 located at the ends of the base 91 along the X-axis, and a workpiece mounting table 99 connected to the shaft support means 93 through a rotating shaft 95 and supported rotatably in the direction indicated by arrow 97 about a horizontal axis extending in the direction along the X-axis. The workpiece mounting table 99 is moved, for rotational indexing in a plurality of positions, by a motor, a toothed clutch (not shown) or the like. Pushing means 101 is located on the base 91 between the bottom of the workpiece mounting table 99 and the base 91 for pushing the workpiece mounting table 99 upwardly. The pushing means 101 imparts an upward pushing force to the workpiece mounting table 99, so that the deformation (deflection) in the direction along the X-axis which is liable to occur when the workpiece mounting table 99 is elongated in the direction along the X-axis is prevented thereby making possible highly accurate machining of the workpiece 89.

The workpiece mounting table 99 of the workpiece support structure 15 shown in FIG. 9 has two opposed workpiece mounting surfaces 103 on which the workpiece 89 is mounted directly or through a pallet 105. The workpiece support structure 15 shown in FIGS. 1 and 9 has the two workpiece mounting surfaces 103, and therefore while the machining process is performed on one of the workpiece mounting surfaces 103 opposite to the spindle support structure 13, the setup process for the workpiece 89 can be carried out on the other workpiece mounting surface 103 in parallel to the machining process on the first workpiece mounting surface 103. Thus, the machine stopping time for the setup process can be minimized for an improved operating rate of the machine.

The pushing means 101 of the workpiece support structure 15 shown in FIG. 9 can be extended and retracted with respect to the base 91. As shown in FIG. 9, for example, the pushing means 101 is constituted by a servo motor 107, a gear 109 rotated by the servo motor 107, a nut 111 rotated by the gear 109 and a push screw 113 in mesh with the nut so that it can be extended and retracted. Such mechanism is known and will not be described in detail herein. The pushing means 101 can of course be made extendable and retractable by use of other mechanisms.

The pushing means 101 which can be extended and retracted as described above moves back toward the base 91 to prevent it from interfering with the rotation of the workpiece mounting table 99 during the rotational indexing of the workpiece mounting table 99, while after the rotational indexing of the workpiece mounting table 99, the pushing means 101 advances toward the bottom of the workpiece mounting table 99 from the base 91 and pushes the workpiece mounting table 99 upwardly. After pushing it upwardly, the pushing force is adjusted by the servo motor so that the deflection of the workpiece mounting table 99 can be substantially eliminated.

Preferably, the workpiece mounting table 99 has truncated conical depressions 115 on the upper and lower sides in FIG. 9, and the push screw 113 having a forward end portion in the shape of a truncated cone is inserted into each depression 115. In such a case, the pushing means 101 has the functions of pushing up the workpiece mounting table 99 and holding the workpiece mounting table 99 at the indexed position. At least one pushing means 101 is located along the X-axis.

A workpiece mounting table 99' of the workpiece support structure 15 according to the second embodiment shown in FIG. 10, unlike the counterpart according to the embodiment shown in FIG. 9, has a semicircular section and a single workpiece mounting surface 103. In such a case, the setup process of the workpiece 89 is carried out on the workpiece mounting surface 103 at its horizontal position, after which the workpiece mounting table 99' is rotated by 90 degrees and rotationally indexed to the machining position indicated by dashed line in FIG. 10. Thus, the setup process is facilitated, with the result that the time required for the setup process can be shortened thereby contributing to an improved efficiency of the machining process.

It should be noted that an inclined portion of the workpiece 89 can be machined by setting the workpiece mounting surface 103 in an inclined position instead of in a vertical position during the machining of the workpiece.

The pushing means 101' shown in FIG. 10 also has a roller 117 pivotally supported at the forward end thereof, and unlike the pushing means 101 shown in FIG. 9, is always in pressure contact with the semicircular outer peripheral surface of the workpiece mounting table 99' through the roller 117. This is because the workpiece mounting table 99' shown in FIG. 10 is required to be rotated only by 90 degrees as described above, and the pushing means 101', even if in contact with the outer peripheral surface of the workpiece mounting table 99', does not interfere with the rotational indexing of the workpiece mounting table 99'.

Figure 11:
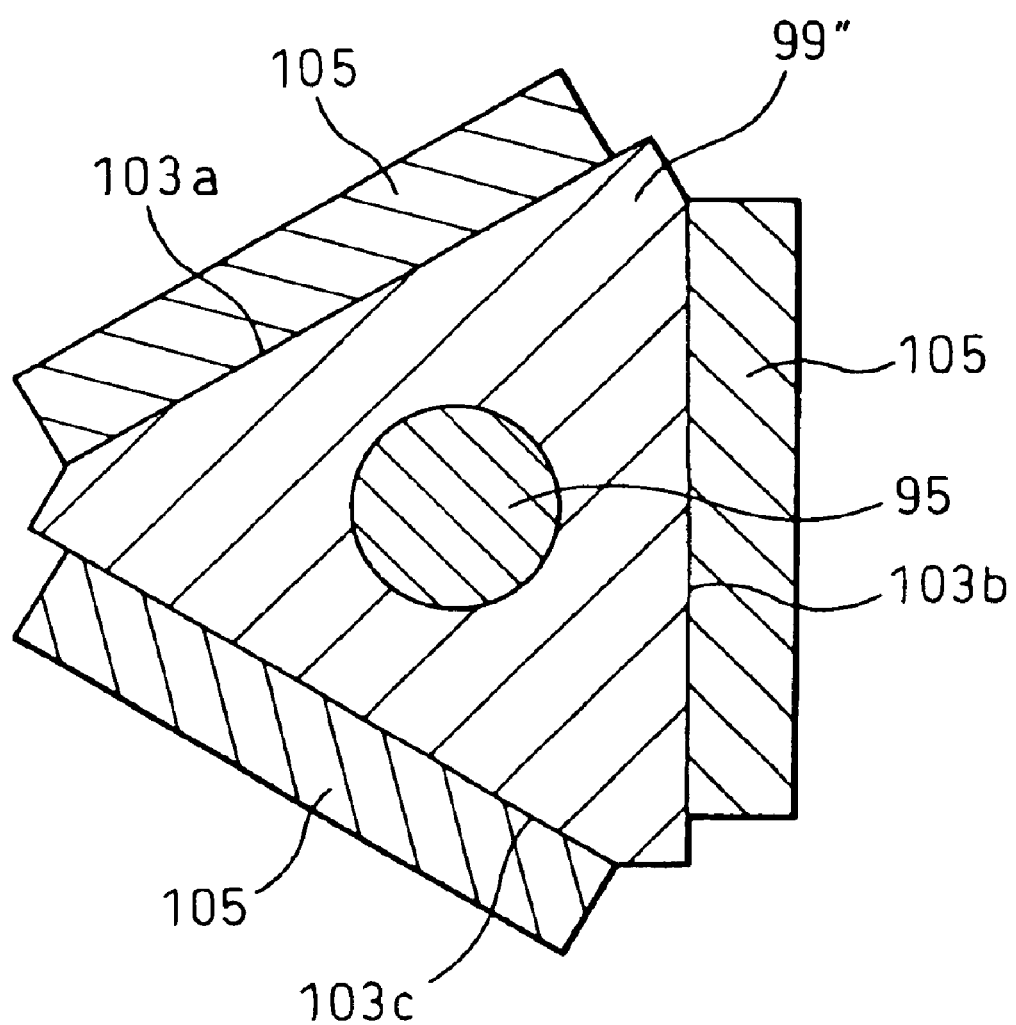
FIG. 11 shows a workpiece mounting table according to a third embodiment of a workpiece support structure.

The workpiece mounting table, as a workpiece mounting table 99" shown in FIG. 11, can be configured of a triangle pole having a section in the shape of a regular triangle with three workpiece mounting surfaces 103a, 103b, 103c. Such a workpiece mounting table 99" has additional advantages of the workpiece holders 99, 99' shown in FIGS. 9 and 10. Specifically, the setup process of the workpiece 89 can be carried out on the first workpiece mounting surface 103a directed 30 degrees upwardly from the horizontal plane, and the machining process can be conducted on the second workpiece mounting surface 103b in vertical position. In this way, the setup process can be carried out during the machining. Further, the setup process can be facilitated by the fact that the first workpiece mounting surface 103a is substantially directed upwardly. In addition, as for the third workpiece mounting surface 103c directed 30 degrees downwardly from the horizontal plane, it has the advantage that the chips and cutting fluid can easily and naturally drop down from the workpiece 89 and be collected when the workpiece 89 is cleaned after being machined. Thus, the machining process is further improved in efficiency.

The workpiece mounting table may be formed in the shape of a polygon pole having at least four workpiece mounting surfaces. In such a case, this workpiece mounting table also has the same advantage as the workpiece mounting table having three workpiece mounting surfaces described above.

The spindle support structure 13 and the workpiece support structure 15 described above are placed with the chip discharge means 17 interposed therebetween as shown in FIG. 1. According to the embodiment shown in FIG. 1, a lift-up chip conveyor is used as the chip discharge means 17 which is driven in the direction along the X-axis to discharge the chips produced in the machining area to the outside of the machining area. The lift-up chip conveyor is known and illustrated in simplified fashion in the drawing.

The chips of the workpiece 89 produced in the machining area, after having naturally dropped onto the horizontal travel unit of the lift-up chip conveyor defined as the chip discharge means 17, are lifted up, separated from the cutting fluid and sequentially discharged out of the machining area. Thus, the job of removing the chips from the machining area after machining the workpiece is reduced.

Further, the spindle support structure 13 and the workpiece support structure 15, which are placed with the chip discharge means 17 interposed therebetween, are not required to be integrated with each other. As a result, the spindle support structure 13 and the workpiece support structure 15 can each be produced in a unit, and if connected in alignment along the X-axis, can meet the requirement for a longer workpiece 89 along the X-axis.

Figure 12:
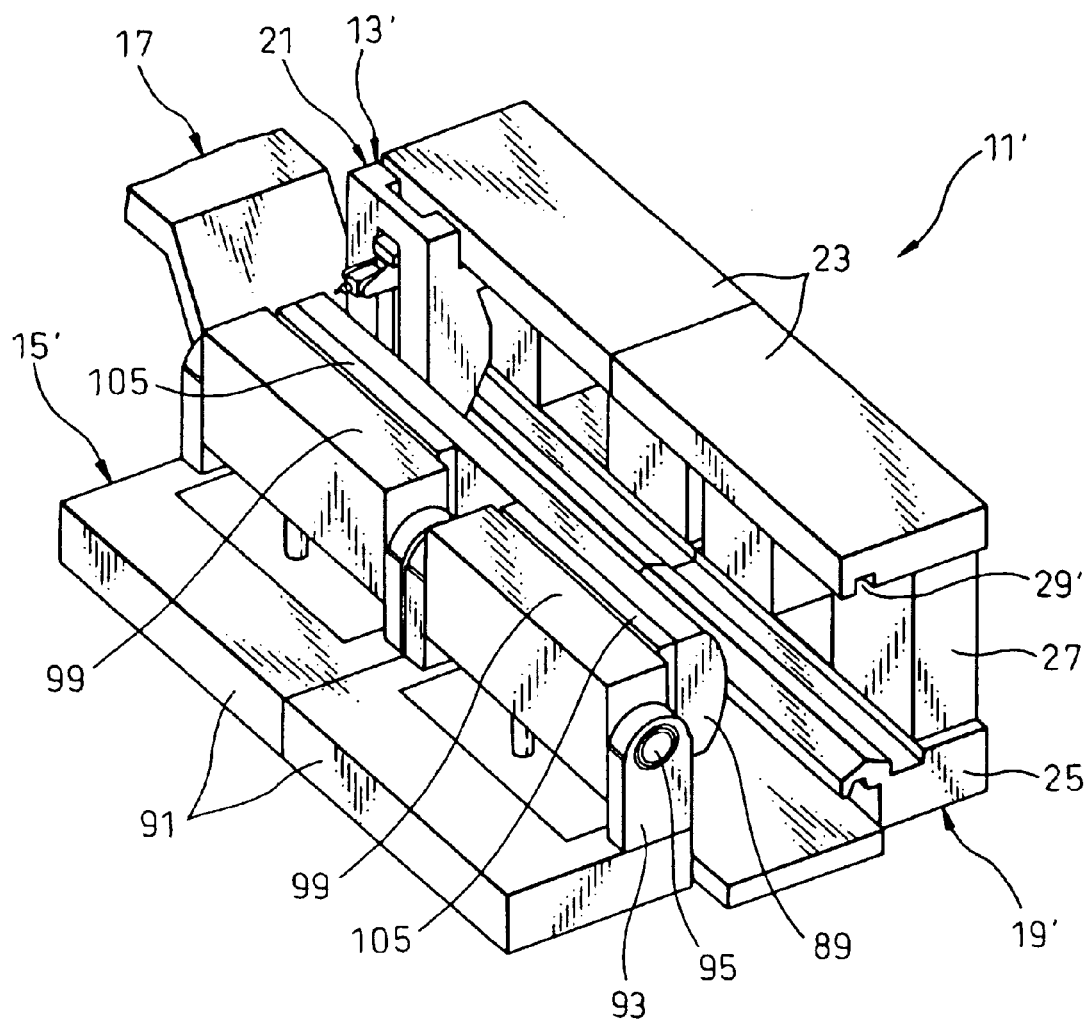
FIG. 12 shows an embodiment of numerically controlled machine tool constituted of modules according to the present invention.

FIG. 12 shows an embodiment of a numerically controlled machine tool 11' constituted of individual modular units according to the present invention.

According to this embodiment, a plurality of the bases 19 of unit length of the spindle support structure 13 shown in FIG. 1 are coupled in the direction along the X-axis to constitute an extended base 19', so that the X-axis guides 43 and the stator 49 of the linear motor located inside of the upper and lower extended longitudinal spaces 29' of the extended base 19', i.e. the track for the X-axis sliders 33 are extended along the X-axis. An extended spindle support structure 13' is constituted such that a single movable 21 moves along the extended track. On the other hand, an extended workpiece support structure 15' is constituted by coupling a plurality of workpiece support structures 15 of unit length with their horizontal axes defined as rotational axes of the workpiece mounting table 99 in alignment with each other. The extended spindle support structure 13' and the extended workpiece support structure 15' thus constituted are placed with the chip discharge means interposed therebetween, so that the numerically controlled machine tool 11' extended along the X-axis is easily manufactured. It should be noted that the chip discharge means can be also extended by constituting the horizontal travel unit thereof in units.

Consequently, this allows a machine tool of a size meeting the demand of the machine tool user to be easily and quickly manufactured. This also prevents each component of the machine tool from being unnecessarily large, thereby facilitating the installation workpiece of the machine tool.

It is noted that in the embodiment shown in FIG. 12, the workpiece 89 is mounted over a plurality of workpiece mounting table 99 constituting units and the rotating direction of the workpiece 89 is limited by the presence of the shaft support means 93. Therefore, the advantage of an improved machine operating rate is lost which otherwise might be obtained by the capability of carrying out the setup process for the workpiece 89 on one of the workpiece mounting surfaces while the workpiece 89 is being machined on the other workpiece mounting surface. However, this problem can be obviated by connecting the workpiece mounting tables 99 by means of connecting members with the shaft support means 93 of the workpiece support structures 15 removed except the outermost ones and by arranging the pushing means 101 at a plurality of points for preventing the deflection of the connected workpiece mounting tables.

By adding a pallet changing means 119 to the numerically controlled machine tool 11 according to the present invention as shown in FIG. 13, the job is facilitated for mounting and changing a pallet 105 carrying a workpiece 89 (not shown in FIG. 13 for simplicity) on the workpiece mounting table 99. FIG. 13 shows, as an example, a pallet changing means 119 combined with a workpiece support structure 15 having a workpiece mounting table 99 of the type shown in FIG. 1. It should be noted that the spindle support structure 13 is omitted in FIG. 13.

Referring to FIG. 13, the pallet changing means 119 includes a pallet stocker 121 arranged adjacent to the workpiece support structure 15 for storing replacable pallets 105, and a pallet carrier 123 for transporting the pallet 105 between the workpiece mounting table 99 and the pallet stocker 121. Z-axis guide rails 125 extending in the direction along the Z-axis are disposed on the right side of the pallet stocker 121 in the drawing. The carrier base 127 can move on the guide rails 125 in the direction along the Z-axis. The pallet carrier 123 is carried onto the carrier base 127 and moves in the direction along the Z-axis to exchange the pallets 105 at various locations with the pallet stocker 121. This exchange is carried out by a cylinder unit 123a located on the top of the pallet carrier 123. A hook for engaging the pallet 105 is located at the forward end of the piston rod of the cylinder unit 123a, so that the pallet 103 is slidably moved between the pallet carrier 123 and the pallet stocker 121 by the extension/contraction of the piston rod to be exchanged with another one. Further, an X-axis guide rail 129 extending in the direction along the X-axis to the front of the workpiece mounting table 99 of the workpiece support structure 15 from the end portion of the Z-axis guide rails 125 are located at the end of the Z-axis guide rails 125. At this end thereof, the pallet carrier 123 can move from the carrier base 127 onto the X-axis guide rail 129.

As a result, it is possible to transfer/receive the pallet 105 with the workpiece 89 mounted thereon between the workpiece support structure 15 and the pallet stocker 121 via the pallet carrier 123. If the pallet mounting means 135 by which the pallet 105 can be automatically mounted or demounted is disposed on the workpiece mounting table 99, the pallet change process which otherwise might consumes a considerable amount of labor can be performed automatically. The pallet mounting means 135 is a known means including a cylinder for pulling the pallet 105 to the workpiece mounting table 99 by engagement at the four corners of the side of the pallet 105 opposed to the side thereof where the workpiece 89 is mounted.

Further, a setup station 131 may be disposed on traveling path for the pallet carrier 123, i.e. on a location along an X-axis guide rail 129 and a Z-axis guide rail 125. The setup station 131 is preferably provided with means 133 for rotating the pallet 105 by 90 degrees between the vertical and horizontal positions thereof to facilitate the setup process. The setup station 131 secures the space for the setup process other than the pallet mounting table 99 of the workpiece support structure 15 and thus enhances the efficiency of the setup process.

Although the present invention has been described above with reference to the embodiments provided with the workpiece mounting table 99 capable of rotational indexing such a workpiece mounting table 99 may be fixed (not rotatable). In other words, the workpiece support structure may be configured as a workpiece rest for fixedly mounting the workpiece thereon.

Although the present invention has been described with reference to several embodiments thereof shown in the accompanying drawings, the embodiments are only illustrative but not limitative. The scope of the present invention should be limited by the appended claims thereof, and the present invention can be changed and modified without departing from the scope of the claims.

| LIST OF REFERENCE CHARACTERS | |
|---|---|
| 11, 11' | Numerically controlled machine tool |
| 13 | Spindle support structure |
| 13' | Extended spindle support structure |
| 15 | Workpiece support structure |
| 15' | Extended workpiece support structure |
| 17 | Chip discharge means |
| 19 | Base |
| 19' | Extended base |
| 21 | Movable body |
| 23 | Beam |
| 25 | Bed |
| 27 | Column |
| 29 | Longitudinal space |
| 29' | Extended longitudinal space |
| 31 | Opening |
| 33 | X-axis slider |
| 35 | Y-axis slider |
| 37 | Z-axis slider |
| 39 | Through opening |
| 41a, 41b | Extension |
| 43 | X-axis guide |
| 45 | Slide element |
| 47 | Mover |
| 49 | Stator |
| 51 | Y-axis guide |
| 53 | Y-axis slide element |
| 55 | Nut |
| 57 | Ball screw |
| 59 | Z-axis guide |
| 61 | Z-axis slide element |
| 63 | Z-axis motor |
| 65 | Non-contact wiper |
| 67 | Non-contact wiper |

-continued

LIST OF REFERENCE CHARACTERS

| | |
|---|---|
| 69 | Contact wiper |
| 71 | Contact wiper |
| 73 | Spindle head |
| 75 | Spindle |
| 77 | Rotational axis |
| 79 | Swivel base |
| 81 | Swivel motor |
| 83 | Gear |
| 85 | C-axis motor |
| 86 | Direction along A-axis |
| 87 | Direction along C-axis |
| 89 | Workpiece |
| 91 | Base |
| 93 | Shaft support means |
| 95 | Rotating shaft |
| 97 | Arrow |
| 99, 99', 99" | Workpiece mounting table |
| 101, 101' | Pushing means |
| 103, 103a, 103b, 103c | Workpiece mounting surface |
| 105 | Pallet |
| 107 | Servo motor |
| 109 | Gear |
| 111 | Nut |
| 113 | Push Screw |
| 115 | Depression |
| 117 | Roller |
| 119 | Pallet changing means |
| 121 | Pallet stocker |
| 123 | Pallet carrier |
| 125 | Z-axis guide rail |
| 127 | Carrier Base |
| 129 | X-axis guide rail |
| 131 | Setup station |
| 133 | Means for rotating |
| 135 | Pallet mounting means |

What is claimed is:

1. A numerically controlled machine tool for machining a workpiece mounted on a workpiece support unit by moving a spindle having a tool mounted thereon in directions along an X-axis, a Y-axis and a Z-axis with respect to the workpiece, said machine tool comprising:

a spindle support structure including a base adapted to be located on a floor surface and having guides extending in the direction along the X-axis on the upper and lower portions thereof, an X-axis slider guided along the guides on the upper and lower portions of said base to move from side to side in the direction along the X-axis, a Y-axis slider guided to move upwardly and downwardly in the direction along the Y-axis on said X-axis slider, a Z-axis slider guided to move forwardly and backwardly in the direction along the Z-axis on said Y-axis slider, and a spindle head mounted to be rotatable about at least a rotational axis extending in a direction along the Z-axis and a rotational axis perpendicular to a direction along the Z-axis;

a workpiece support structure including a base having shaft support means located at the opposing ends thereof along the X-axis, and a workpiece mounting table supported by said shaft support means to allow for rotational indexing about a horizontal axis extending in the direction along the X-axis, said workpiece mounting table having at least one workpiece mounting surface; and a chip discharge means located between said spindle support structure and said workpiece support structure for discharging chips produced in the machining area to the outside of said machining area, wherein said base of said spindle support structure has longitudinal spaces extending in the direction along the X-axis and opening downwardly in the upper and lower portions of said base, respectively, and each of said longitudinal spaces accommodates therein a guide for guiding and supporting said X-axis slider and an X-axis feed means for moving said X-axis slider in the direction along the X-axis.

2. The numerically controlled machine tool according to claim 1, wherein said base of said spindle support structure comprises an extended base having a plurality of base units coupled to each other along the X-axis, said base unit having a predetermined X-axis unit length, and said workpiece support structure comprises an extended workpiece support structure having a plurality of workpiece support structure units coupled to each other along the X-axis with the horizontal axes thereof aligned, said workpiece support structure having a predetermined X-axis unit length.

3. The numerically controlled machine tool according to claim 1, wherein said X-axis slider of said spindle support structure is driven in the direction along the X-axis by linear motors disposed along said guides on the upper and lower portions of said base, respectively, and said linear motor includes a stator and a mover arranged on said base and said X-axis slider in opposed relation to each other so that an attraction force of said stator acting on said mover reduces the load in gravitational direction exerted on said guide of said X-axis slider.

4. The numerically controlled machine tool according to claim 1, wherein said workpiece mounting table of said workpiece support structure is formed into a shape of a substantially triangle pole having three workpiece mounting surfaces extending in parallel to the horizontal axis in the direction along the X-axis.

5. The numerically controlled machine tool according to claim 1, wherein said workpiece support structure is provided with a pushing means located between the bottom of said workpiece mounting table and said base for imparting an upward pushing force on said workpiece mounting table.

6. A numerically controlled machine tool for machining a workpiece mounted on a workpiece support unit by moving a spindle having a tool mounted thereon in directions along an X-axis, a Y-axis and a Z-axis with respect to the workpiece, said machine tool comprising:

a spindle support structure including a base adapted to be located on a floor surface and having guides extending in the direction along the X-axis on the upper and lower portions thereof, an X-axis slider guided along the guides on the upper and lower portions of said base to move from side to side in the direction along the X-axis, a Y-axis slider guided to move upwardly and downwardly in the direction along the Y-axis on said X-axis slider, a Z-axis slider guided to move forwardly and backwardly in the direction along the Z-axis on said Y-axis slider, and a spindle head mounted to be rotatable about at least a rotational axis extending in a direction along the Z-axis and a rotational axis perpendicular to a direction along the Z-axis;

a workpiece support structure including a base having shaft support means located at the opposing ends thereof along the X-axis, and a workpiece mounting table supported by said shaft support means to allow for rotational indexing about a horizontal axis extending in the direction along the X-axis, said workpiece mounting table having at least one pallet mounting means for detachably mounting on said workpiece mounting table a pallet for attaching a workpiece thereon;

a pallet changing means including a pallet stocker located adjacent to said workpiece support structure and a pallet carrier for transporting the pallet between said workpiece mounting table and said pallet stocker; and a chip discharge means located between said spindle support structure and said workpiece support structure for discharging chips produced in the machining area to the outside of said machining area, wherein said base of said spindle support structure has longitudinal spaces extending in the direction along the X-axis and opening downwardly in the upper and lower portions of said base, respectively, and each of said longitudinal spaces accommodates therein a guide for guiding and supporting said X-axis slider and an X-axis feed means for moving said X-axis slider in the direction along the X-axis.

7. A numerically controlled machine tool for machining a workpiece mounted on a workpiece support unit by moving a spindle having a tool mounted thereon in directions along an X-axis, a Y-axis and a Z-axis with respect to the workpiece, said machine tool comprises:

a spindle support structure including a base adapted to be located on a floor surface and having guides extending in the direction along the X-axis on the upper and lower portions thereof, an X-axis slider guided along the guides on the upper and lower portions of said base to move from side to side in the direction along the X-axis, a Y-axis slider guided to move upwardly and downwardly in the direction along the Y-axis on said X-axis slider, a Z-axis slider guided to move forwardly and backwardly in the direction along the Z-axis on said Y-axis slider, and a spindle head fixedly mounted on said Z-axis slider or mounted to be rotatable in at least one of directions along an A-axis, a B-axis and a C-axis; and a workpiece rest disposed in the front of said spindle support structure for fixedly mounting a workpiece thereon, wherein said base of said spindle support structure is provided with longitudinal spaces extending in the direction along the X-axis and opening downwardly in the upper and lower portions of said base, respectively, the guide located in each of said longitudinal spaces for guiding and supporting said X-axis slider, and an X-axis feed means located along said guide in each of said longitudinal spaces for moving said X-axis slider.

8. The numerically controlled machine tool according to claim 7, wherein said X-axis feed means comprises a linear motor including a stator, and said X-axis slider is provided with wiper means for removing dusts or chips attached to said guide and the stator of said linear motor.

9. The numerically controlled machine tool according to claim 7, wherein said X-axis feed means comprises a linear motor including a stator and a mover arranged on said base and said X-axis slider, respectively, in opposed relation to each other so that an attraction force of said stator acting on said mover reduces the load, in the gravitational direction, exerted on said guide of said X-axis slider.

10. A numerically controlled machine tool for machining a workpiece mounted on a workpiece support unit by moving a spindle having a tool mounted thereon in directions along an X-axis, a Y-axis and a Z-axis with respect to the workpiece, said machine tool comprising:

a spindle support structure including a base adapted to be located on a floor surface and having guides extending in the direction along the X-axis on the upper and lower portions thereof, an X-axis slider guided along the guides on the upper and lower portions of said base to move from side to side in the direction along the X-axis, a Y-axis slider guided to move upwardly and downwardly in the direction along the Y-axis on said X-axis slider, a Z-axis slider guided to move forwardly and backwardly in the direction along the Z-axis on said Y-axis slider, and a spindle head mounted to be rotatable about at least a rotational axis extending in a direction along the Z-axis and a rotational axis perpendicular to a direction along the Z-axis;

a workpiece support structure including a base having shaft support means located at the opposing ends thereof along the X-axis, and a workpiece mounting table supported by said shaft support means to allow for rotational indexing about a horizontal axis extending in the direction along the X-axis, said workpiece mounting table having at least one workpiece mounting surface; and a chip discharge means located between said spindle support structure and said workpiece support structure for discharging chips produced in the machining area to the outside of said machining area, wherein said X-axis slider of said spindle support structure is driven in the direction along the X-axis by linear motors disposed along said guides on the upper and lower portions of said base, respectively, and each of said linear motors includes a stator and a mover arranged on said base and said X-axis slider in opposed relation to each other so that an attraction force of said stator acting on said mover reduces the load in gravitational direction exerted on said guide of said X-axis slider.

11. A numerically controlled machine tool for machining a workpiece mounted on a workpiece support unit by moving a spindle having a tool mounted thereon in directions along an X-axis, a Y-axis and a Z-axis with respect to the workpiece, said machine tool comprising:

a spindle support structure including a base adapted to be located on a floor surface and having guides extending in the direction along the X-axis on the upper and lower portions thereof, an X-axis slider guided along the guides on the upper and lower portions of said base to move from side to side in the direction along the X-axis, a Y-axis slider guided to move upwardly and downwardly in the direction along the Y-axis on said X-axis slider, a Z-axis slider guided to move forwardly and backwardly in the direction along the Z-axis on said Y-axis slider, and a spindle head mounted to be rotatable about at least a rotational axis extending in a direction along the Z-axis and a rotational axis perpendicular to a direction along the Z-axis; and a workpiece rest disposed in the front of said spindle support structure for fixedly mounting a workpiece thereon, wherein said X-axis slider of said spindle support structure is driven in the direction along the X-axis by linear motors disposed along said guides on the upper an lower portions of said base, respectively, and each of said linear motors includes a stator and a mover arranged on said base and said X-axis slider in opposed relation to each other so that an attraction force of said stator acting on said mover reduces the load in gravitational direction exerted on said guide of said X-axis slider.

* * * * *